United States Patent [19]

O'Connor et al.

[11] 4,353,152
[45] Oct. 12, 1982

[54] PULSE RATE MONITOR

[75] Inventors: Arthur H. O'Connor, Lancaster; Robert A. Rossman, Leola, both of Pa.

[73] Assignee: Novatec, Inc., Lancaster, Pa.

[21] Appl. No.: 123,351

[22] Filed: Feb. 21, 1980

[51] Int. Cl.³ .............................................. A61B 5/02
[52] U.S. Cl. .................................... 128/689; 128/666
[58] Field of Search ....................... 128/633, 665–667, 128/687–690, 706

[56] References Cited

U.S. PATENT DOCUMENTS

| | | | |
|---|---|---|---|
| 3,908,636 | 9/1975 | Page | 128/666 |
| 3,980,075 | 9/1976 | Heule | 128/666 |
| 4,063,551 | 12/1977 | Sweeney | 128/666 |
| 4,116,228 | 9/1978 | Hudspeth et al. | 128/666 |
| 4,166,454 | 9/1979 | Meijer | 128/666 |
| 4,181,134 | 1/1980 | Mason et al. | 128/706 X |
| 4,201,222 | 5/1980 | Haase | 128/666 |
| 4,230,127 | 10/1980 | Larson | 128/690 X |
| 4,258,719 | 3/1981 | Lewyn | 128/690 |

Primary Examiner—Robert W. Michell
Assistant Examiner—Francis J. Jaworski
Attorney, Agent, or Firm—Martin Fruitman

[57] ABSTRACT

A pulse rate monitor for use while exercising. A clothespin type finger clip remote from the counting and display unit grips the user's finger in a predictable, mechanically stable manner. A light emitting diode, strobed to reduce battery drain, transmits infrared radiation through the finger, and electronic circuitry monitors the modulation of radiation caused by changes in capillaries with each heart beat. The circuitry includes an active load for the phototransistor, which, by means of bandpass filtered feedback, enhances heart beat signal and reduces sensitivity to ambient light, noise, and variations in phototransistor characteristics.

2 Claims, 4 Drawing Figures

PULSE RATE MONITOR

BACKGROUND OF THE INVENTION

The present invention deals generally with human function measurement apparatus and more specifically with a pulse rate monitor device made specifically for use while participating in strenuous physical activity, such as exercise.

Current medical technology indicates that monitoring of the human pulse rate can yield valuable diagnostic information. Moreover, pulse rate monitoring is an important factor in regulating a meaningful exercise program designed to strengthen the pulmonary and cardiovascular systems. In such an exercise program, it is important to exercise to a level which significantly increases the pulse rate but to limit that increase in pulse rate to prescribed levels to prevent over-stressing the body functions too early in the program. Yet the conventional method of pulse monitoring, counting the pulse for a period of time, requires pausing in activity. Such monitoring is therefore unsuitable in that it measures the pulse after the exercise, not during it.

Ironically, however, pulse rate monitoring with accuracy equal to the ultimate in the electronics art is also not fully satisfactory to the individual on such an exercise program. For instance, a pulse rate measurement made by measuring the time between two pulse beats, however accurate, yields results which have little medical significance. Because there is considerable variation in an individual's pulse-to-pulse timing and because short-term patterns are noticeable in such pulse-to-pulse times, a useable rate monitor must to some degree duplicate the traditional method of medical pulse-taking which is an average of pulses taken over some period of multiple pulse beats. Only such a measurement allows the monitoring of pulse rate to be tied in to an individual's medical history and to medical technology in general.

Several pulse rate monitoring systems are known, for instance, U.S. Pat. No. 3,908,636, No. 4,030,483 and No. 4,063,551. This prior art, however, is unable to accurately detect, process and display in a simple format, the pulse rate of a user under actual conditions of use while exercising.

It is, therefore, an object of this invention to yield a personal pulse rate monitor which accurately and conveniently indicates the heart beat rate to a user while the user is actually engaging in strenuous physical activity such as bicycling.

It is another object of this invention to measure the pulse rate in such a manner that the results are consistent with prior methods used by the medical profession, so that previous diagnostic techniques may continue to be used.

It is a still further object of this invention to furnish a sensor contact system which is independent of variations caused by the user's grip or the particular activity of the user.

SUMMARY OF THE INVENTION

These objectives are fulfilled by the finger clamping, highly portable pulse rate monitor of the present invention. The system is small, portable, and uses a highly accurate electronic current to average four heart beat periods and display the heart beat rate in digital format.

The preferred embodiment of the Pulse Rate Monitor is essentially a package the size of a small hand held electronic calculator with a finger clamping sensor unit attached to the display unit by means of a short flexible cable.

The finger clamp is opened by pressure on one end, much like a spring loaded clothes pin, and the user's finger is inserted within a recess preformed in light shielding material within the clamp portion of the unit. Within the sensor unit a light emitting diode and a photo-transistor are mounted in close proximity so that the capillaries of the finger affect the light transmission between them.

This specific configuration has distinct advantages in typical use. First, and most important, the contact with the radiation source and sensor is not determined by force applied by the user, but rather by the tension of a spring specified by the instrument manufacturer. The contact is thus optimized for consideration of signal pickup quality, and does not vary with individual users. Moreover, since the contact does not depend on the user's grip, the contact is essentially constant regardless of the user's activity and thus another source of extraneous signal is eliminated.

Another advantage, particularly pertinent in many forms of exercise, is that the user can, for many activities, use his hands with very little restriction, and need not grip the instrument in his palm. For instance, the present invention, when used with a bicycle, permits normal activity with the display unit attached to the handlebars in clear view.

One particular benefit of the electronic circuit of the invention is that the light emitting diode and phototransistor are strobed or pulse activated, rather than constantly powered, to permit higher peak light intensities and higher signal gain while conserving battery power. The duty factor on the system, the time it is activated relative to total time, is easily reduced to 20 percent, thus dramatically reducing the battery drain.

One circuit innovation is an active load for the phototransistor which maintains prescribed operating conditions for the phototransistor despite variations in phototransistor sensitivities and ambient light conditions. Another feature of the electronic circuit is a diode feedback circuit in the first amplifier stage which favors amplification of the prescribed signal from the phototransistor, but electronically filters out ambient light signals. Other electronic features include a five heartbeat period averaging system based upon a ramp voltage build-up by constant current charging of a capacitor. A low battery voltage warning system included in the circuitry is designed to light all the decimal points of the digital display to warn the user of potential inaccuracies in readings due to lowered battery voltage.

DETAILED DESCRIPTION OF THE INVENTION

MECHANICAL CONFIGURATION OF THE PREFERRED EMBODIMENT

Figure 1:
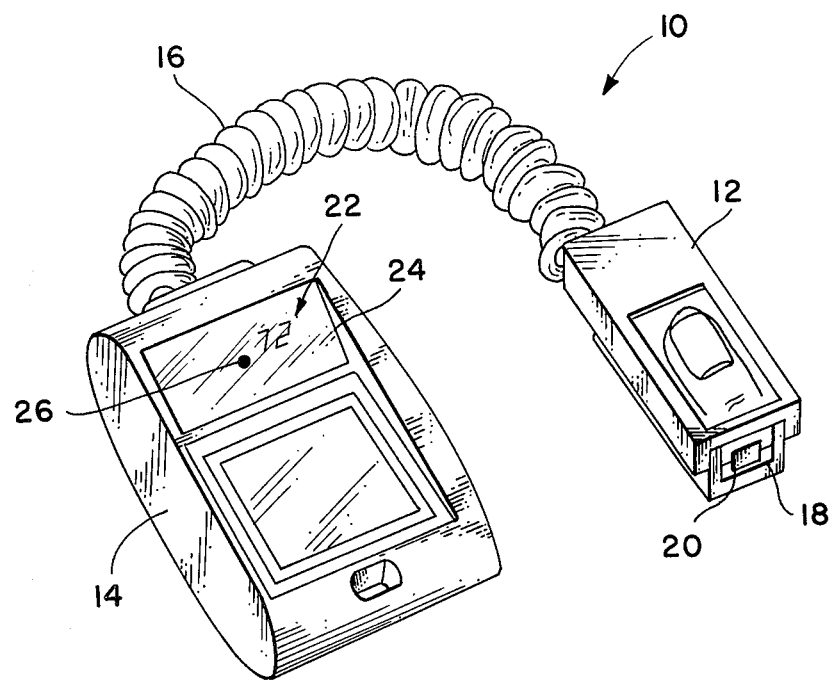
FIG. 1 is a perspective view of the mechanical configuration of the invention.

The mechanical configuration of the pulse rate monitor as shown in FIG. 1 is particularly intended to minimize erroneous signal caused by relative movement between the pulse rate monitor and the user's body, whether caused by differences between users or by the activity being performed by the user.

Pulse rate monitor 10 comprises remote sensing assembly 12, essentially a spring loaded finger clip, and display unit 14 interconnected by flexible cable 16. Remote sensing assembly 12 is constructed with opening 18 which contains preformed recess 20 which clamps and seals around the user's finger and prevents leakage of ambient light into the area of the phototransistor.

A pressure sensitive switch contained within assembly 12 turns the unit on automatically when a finger is clamped into assembly 12 and off when the finger is removed.

Display unit 14 contains all the electronic circuitry except the light emitting diode, the phototransistor and the on-off switch. Digital display 22 is visible in window 24 and indicator dot 26 is activated with each pulse beat to show proper acquisition of signal.

OPERATION OF THE PREFERRED EMBODIMENT

Figure 2:
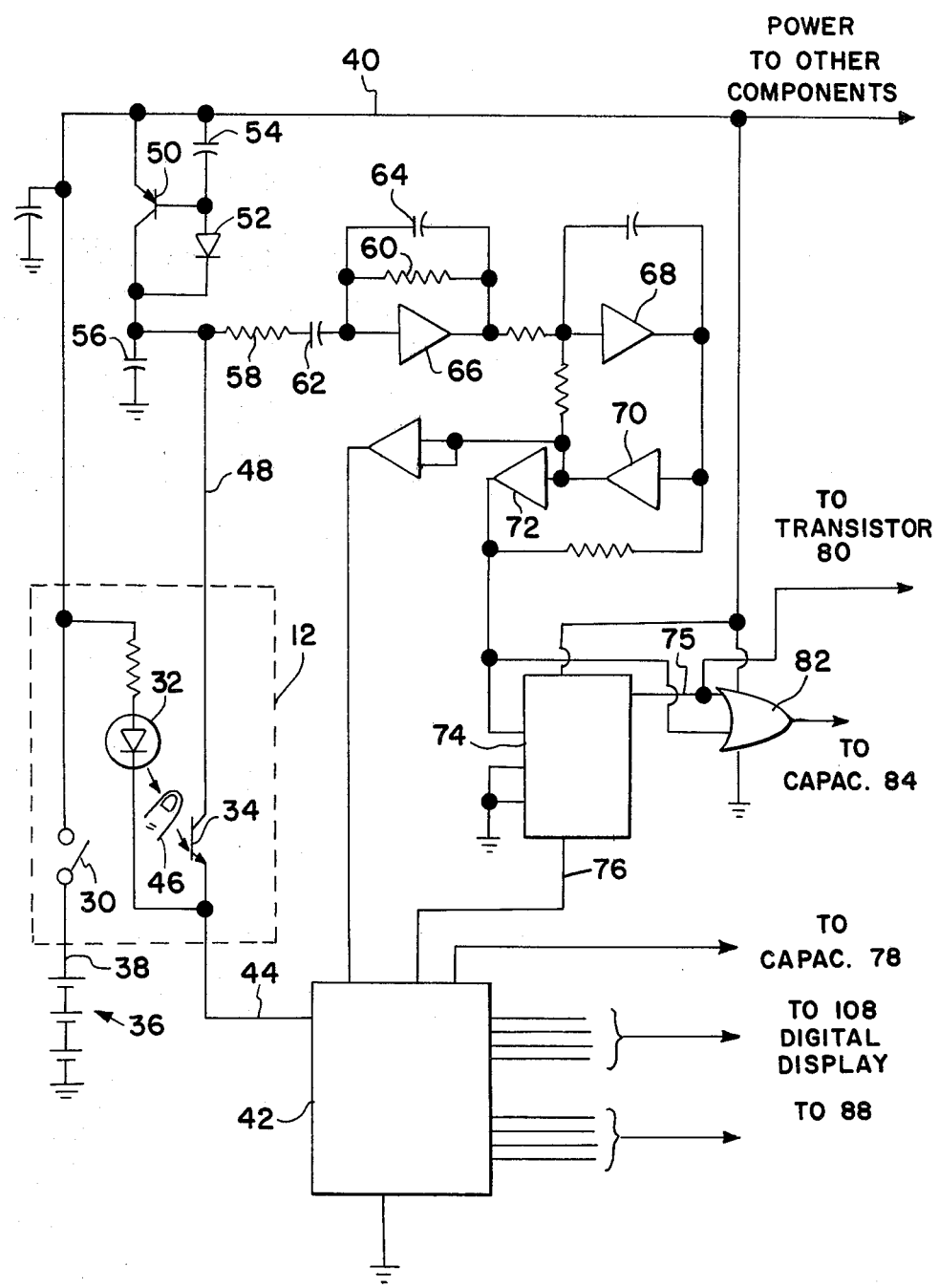
FIG. 2 is part of the electronic circuit diagram of the invention showing the first several stages in the signal path.
Figure 3:
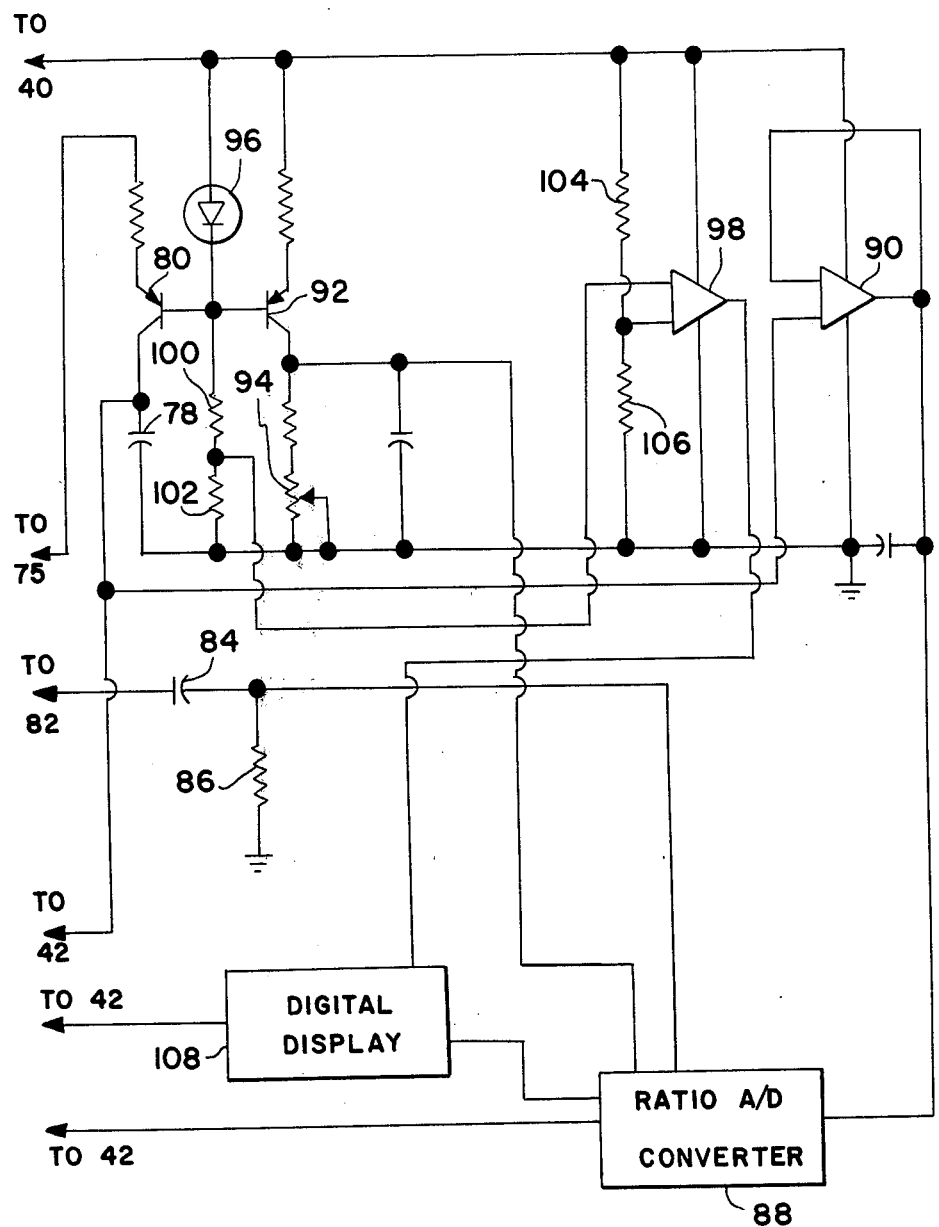
FIG. 3 is part of the electronic circuit diagram of the invention showing the counting stages of the circuit.

As shown in FIGS. 2 and 3, a circuit diagram of the pulse rate monitor shown in two parts, remote sensing assembly 12 contains pressure sensitive on-off switch 30, light emitting diode 32 and phototransistor 34. Switch 30, connected to batteries 36 through line 38, powers the entire unit by means of line 40. Light emitting diode 32 and phototransistor 34 are strobed, pulse actuated, from digital driver 42 through line 44. The signal resulting from modulation of the radiation transmitted between light emitting diode 32 and phototransistor 34 by finger 46 is transmitted to the signal processing circuit stages by line 48. Lines 38, 40, 44 and 48 are all contained in flexible cable 16 which interconnects remote sensing assembly 12 and display unit 14, which contains batteries 36 and all other circuit components.

The strobe action which pulses light emitting diode 32 and phototransistor 34 is attained by the use of strobe rate generator in digital driver 42. Since the digital driver already includes a pulse generator used for the digital display, the left most digit's drive, otherwise unused, is connected through line 44 to light emitting diode 32 and phototransistor 34. This yields an approximate 1K Hertz drive signal with 20% duty factor.

Phototransistor 34 is connected, via line 48, to an active load formed by transistor 50, diode 52 and capacitor 54. Feedback current through diode 52, connected between the base and collector of transistor 50, forces the average collector current of transistor 50 to equal the average collector current of phototransistor 34. This establishes the quiescent operating voltage at transistor 50 collector at approximately one volt below the supply voltage and this voltage remains essentially constant over a wide range of variations of sensitivity and ambient light conditions for phototransistor 34.

Capacitor 54 significantly reduces the feedback current to transistor 50 at frequencies in the range of 0.5 Hz to 3 Hz which are those in the heartbeat range. This increases the collector impedance of transistor 50 and therefore also increases the voltage swing caused by input signals in the heartbeat range of frequencies. Because of the unidirectional current flow forced by diode 52, the feedback action is less for positive voltage swings at the collector of transistor 50, thereby providing enhancement of heartbeat related signals. This results because the origin of heart pulse signals is increased capillary flow in finger 46 which reduces light transmitted from light emitting diode 32 to phototransistor 34, reducing current in phototransistor 34, and causing a positive going voltage at the collector of transistor 50. This action greatly enhances the ability of the circuit to pick up legitimate pulse rate signals and reject noise signals since noise signals generally result from ambient light which increases the current in phototransistor 34.

The 1 KHz strobe signal imposed upon light emitting diode 32 and phototransistor 34 in order to permit operation with higher gain without increase in battery current is filtered out of the signal path by capacitor 56 and does not affect the signal path.

Resistors 58 and 60 and capacitors 62 and 64, along with amplifier 65, further filter and amplify the heart pulse signal. Amplifiers 68, 70 and 72 and their associated components then act as Schmitt triggers to square off the pulse signal for further processing by counter circuit 74 which acts as a central processing unit for the system.

Figure 4:
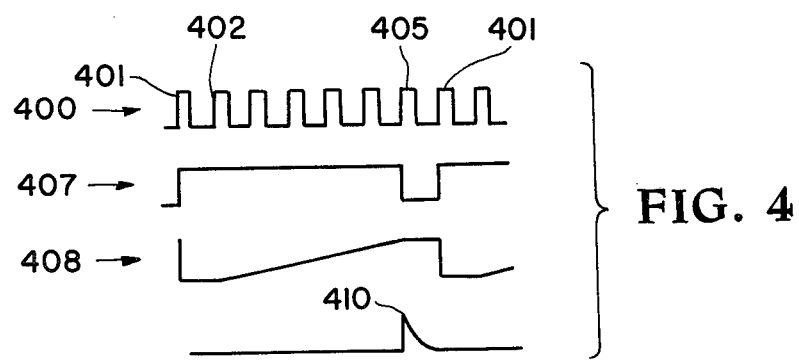
FIG. 4 is a timing diagram of the operation of the invention.

As shown in FIG. 4, a timing diagram of the system, initial pulse 401 of pulse train 400, resets the counter and sets carry out output 407 (line 75 on FIG. 2) and the zero count output high.

The zero count output connected by line 76 (FIG. 2) to digital driver 42 (FIG. 2) turns on a circuit within digital driver 42 which discharges capacitor 78 (FIG. 3).

As second pulse 402 of pulse train 400 causes the zero count of counter 74 to go low, capacitor 78 is permitted to charge through the constant current circuit of transistor 80 (FIG. 3). As shown in timing diagram FIG. 4, voltage 408 on capacitor 78 is permitted to charge for the time until seventh pulse 405. At seventh pulse 405, carry out output 407 goes low, reverse biasing transistor 80, and stops the charging of capacitor 78. Voltage 408 on capacitor 78 is thus raised to a level proportional to the total time elapsed between the beginning of second pulse 402 and the beginning of seventh pulse 405, thereby totaling the time for five pulse periods.

The next pulse 401 into the circuit is used to reset counter 74 and begin the sequence again.

Carry out output 407 (line 75 on FIG. 2) and the pulse input to counter 74 are compared by NOR gate 82 and the resulting pulse out, at the trailing edge of seventh pulse 405, is differentiated by capacitor 84 and resistor 86 (FIG. 3) to yield pulse 410 on timing diagram FIG. 4. Pulse 410 is used to pulse A to D converter 88 which is connected in the ratio mode with voltage 408 connected to the reference input via voltage follower 90, and a calibration voltage from transistor 92 connected to the normal input.

When pulsed, decoded and displayed the output of A to D converter 88 is equal to a fixed number times the calibration voltage divided by voltage 408 of capacitor 78. The calibration voltage, adjustable by resistor 94, can thus be set so that the display equals the heart pulse rate in beats per minute.

Two additional features of the invention are also shown in FIG. 3.

Transistors 80 and 92 and light emitting diode 96 are used in a unique circuit configuration to form two constant current sources which track in temperature and mutually compensate for changes in the charging source of capacitor 78, which is the time measurement, and the calibration voltage to which the time measurement voltage is compared. This compensation results because the temperature caused change in base to emitter voltage of the silicon PNP transistors 80 and 92 is approximately the same as the temperature caused change in voltage across the gallium arsenide light emitting diode 96.

Amplifier 98 is used in a unique circuit to indicate a battery voltage which is lower than desired. Amplifier 98 compares the voltage between resistors 100 and 102 with the voltage between resistors 104 and 106. Since the voltage across light emitting diode 96 is relatively independent of current as battery voltage drops, the voltage at the junction of resistors 100 and 102 will fall more rapidly than the voltage at the junction of resistors 104 and 106 which are connected directly to line 40 and batteries 36. Thus, at some battery voltage, the non-inverting input of amplifier 98 will become more positive than the inverting input, and the output will go high. This high output, connected to digital display 108 at the decimal points input 110, turns on all the decimal point indicators of digital display 108 and clearly indicates a low battery voltage.

It is to be understood that the form of this invention as shown is merely a preferred embodiment. Various changes may be made in the function and arrangement of parts; equivalent means may be substituted for those illustrated and described; and certain features may be used independently from others without departing from the spirit and scope of the invention as defined in the foregoing claims.

What is claimed as new and desired to be secured by Letters Patent of the United States is:

1. In a portable heart pulse rate monitor device of the type having a radiation source in proximity to a radiation sensor with the transmission of radiation between the source and sensor modulated by capillary blood flow of a finger placed in proximity to both the radiation source and radiation sensor; an electronic circuit to power the radiation source and radiation sensor and to amplify and process the sensor's output signal; and a display means to furnish the user with a direct reading of the user's pulse rate in beats per minute, the improvement comprising: a phototransistor acting as the radiation sensor and an active load connected to the phototransistor, the active load comprising a transistor with a unidirectional feedback circuit, connected between base and collector of the transistor, which favors signal variations from the quiescent operating level resulting from reductions in radiation received by the phototransistor, as opposed to signals resulting from increase in radiation to the phototransistor.

2. In a portable heart pulse rate monitor device of the type having a radiation source in proximity to a radiation sensor with the transmission of radiation between the source and sensor modulated by capillary blood flow of a finger placed in proximity to both the radiation source and radiation sensor; an electronic circuit to power the radiation source and radiation sensor and to amplify and process the sensor's output signal; and a display means to furnish the user with a direct reading of the user's pulse rate in beats per minute, the improvement comprising: a constant current source within the electronic circuit connected to and charging a capacitor to convert the sum of time periods between heart beat pulses into a measurable voltage, the constant current source comprising a PNP transistor and emitter connected to a counter circuit, collector connected to the capacitor, and base connected to a temperature compensating circuit;

a counter circuit, connected to the radiation sensor by means of amplifiers and filter means, regularly initiating a count of a specific number of heart beat signal pulses received from the radiation sensor, and connected to and controlling the constant current source;

a calibration voltage source connected to the battery comprising a PNP transistor with variable resistor collector load;

a temperature compensating circuit comprising a light emitting diode connected to the base of the calibration circuit transistor and the base of the constant current source transistor, the light emitting diode selected to have temperature characteristics matching those of the PNP transistor;

an analog to digital converter circuit connected to the constant current source charged capacitor and the calibration voltage source; and a digital driver circuit connected to the analog to digital converter circuit and to a digital display means.

* * * * *